(12) United States Patent
Buzluhan

(10) Patent No.: US 6,982,360 B2
(45) Date of Patent: Jan. 3, 2006

(54) PANTYLINER FOR WOMEN, IN PARTICULAR FOR PREGNANT WOMEN

(76) Inventor: Hülya Buzluhan, Dorfäckerstrasse 39, D-90427 Nürnberg (DE)

(*) Notice: Subject to any disclaimer, the term of this patent is extended or adjusted under 35 U.S.C. 154(b) by 107 days.

(21) Appl. No.: 10/182,011

(22) PCT Filed: Jan. 22, 2001

(86) PCT No.: PCT/DE01/00251
§ 371 (c)(1),
(2), (4) Date: Nov. 1, 2002

(87) PCT Pub. No.: WO01/54642
PCT Pub. Date: Aug. 2, 2001

(65) Prior Publication Data
US 2003/0133173 A1 Jul. 17, 2003

(30) Foreign Application Priority Data
Jan. 24, 2000 (DE) .................... 200 01 141

(51) Int. Cl.
A61F 13/15 (2006.01)

(52) U.S. Cl. .............. 604/362; 604/361; 600/361; 600/362; 600/309; 600/584

(58) Field of Classification Search ........ 604/360–362; 604/424/10.3, 402, 430, 443; 600/309, 361, 600/362, 367, 584, 573

See application file for complete search history.

(56) References Cited

U.S. PATENT DOCUMENTS

| | | | | |
|---|---|---|---|---|
| 5,468,236 A | * | 11/1995 | Everhart et al. | 604/361 |
| 5,823,953 A | | 10/1998 | Richards et al. | |
| 5,876,389 A | | 3/1999 | Morin et al. | |
| 6,126,597 A | * | 10/2000 | Smith et al. | 600/362 |
| 6,149,590 A | * | 11/2000 | Smith et al. | 600/367 |
| 6,374,415 B1 | * | 4/2002 | Lenart | 2/114 |
| 6,436,055 B1 | * | 8/2002 | Roe | 600/584 |

FOREIGN PATENT DOCUMENTS

| | | |
|---|---|---|
| DE | 30 35 902 | 4/1981 |
| DE | 295 14 562 | 11/1995 |
| GB | 2 022 423 | 12/1979 |
| WO | WO94/24557 | 10/1994 |
| WO | WO00/04822 | 2/2000 |

* cited by examiner

*Primary Examiner*—Jacqueline F. Stephens
(74) *Attorney, Agent, or Firm*—Collard & Roe, P.C.

(57) ABSTRACT

The invention relates to a pantyliner, in particular for pregnant women, with a liquid-impermeable lower layer and a liquid-permeable covering layer, where a test insert (3) provided with a test substance is arranged between the lower layer (1) and the covering layer (2).

16 Claims, 3 Drawing Sheets

PANTYLINER FOR WOMEN, IN PARTICULAR FOR PREGNANT WOMEN

CROSS REFERENCE TO RELATED APPLICATIONS

Figure 1:
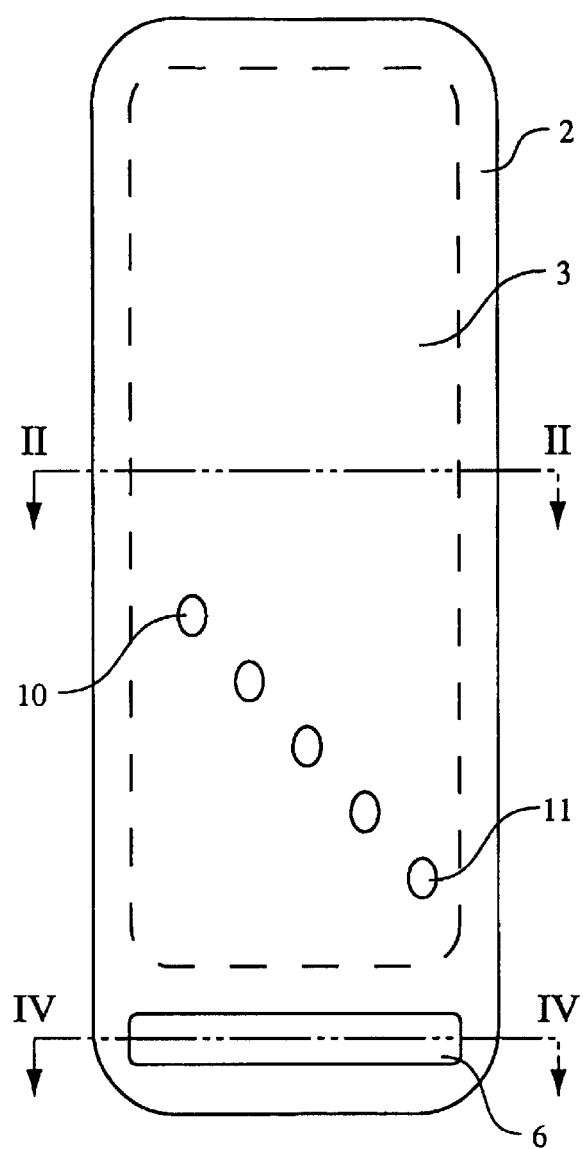

Applicant claims priority under 35 U.S.C. §119 of German Application No. 200 01 141.3 filed Jan. 24, 2000. Applicant also claims priority under 35 U.S.C. §365 of PCT/DE01/00251 filed Jan. 22, 2001. The international application under PCT article 21(2) was not published in English.

DESCRIPTION

The invention relates to a pantyliner having the features of the precharacterizing clause of Patent claim 1.

As prior art, it is, for example, known to medically investigate pregnant women regularly in the vaginal area and to chemically analyse the secretions which arise therein. In this connection, for example, the pH in the vaginal area is regularly determined using litmus test strips in order, for example, to enable detection of undesired premature amniorrhexis of the amniotic sac, during which the pH noticeably changes relative to the state prior to amniorrhexis. If premature amniorrhexis is thereby detected, birth may be induced by the attending doctor. If such premature amniorrhexis is not recognized, this may lead to health risks for the child and mother and, in extreme cases, lead to miscarriage.

The object of the invention is to provide a pantyliner, in particular for pregnant women, with which the risk of a delayed diagnosis of secretions in the vaginal area is reduced or eliminated completely.

This object is achieved by the features of the characterizing clause of Patent claim 1 in conjunction with the features of the precharacterizing clause. Advantageous embodiments of the invention are realized by the dependent claims 2–20.

The pantyliner according to the invention has at least one integrated test insert provided with a test substance, by means of which, for example, secretions of a pregnant woman in the vaginal area and thus, in particular, premature amniorrhexis, can be detected by the pregnant woman herself without a medical examination. Here, the test insert is located below a covering layer of the pantyliner, thus avoiding direct contact with the skin and possible skin irritations.

In cases of premature amniorrhexis, as a result of the secreted amniotic fluid, the vaginal pH changes and shifts from pH 5 (value for vaginal secretion) to about pH 7.5 (value for amniotic fluid).

If litmus paper is used as the test insert, it changes colour, so that premature amniorrhexis can be detected by the pregnant woman herself, and the pregnant woman can consult a doctor as soon as possible. Undiscovered premature amniorrhexis with the described consequences for mother and child can thus be avoided.

By designing the covering layer, which covers the test insert, to be transparent or translucent at least in parts, it is possible to detect a change in the colour of the test insert due to absorbed secretions through the covering layer without the test insert having to be removed from the pantyliner.

If the pantyliner is provided with two or more different test substances, multiple examination and analysis of the secretions in the vaginal area can take place. As well as being able to detect premature amniorrhexis by establishing a change in the pH, it is thus also possible to establish a change in, for example, the sugar or protein contents in the urine.

If a single test insert is used, this may have areas which are provided with different test substances. These areas may be arranged in the form of strips, it also being possible for areas of the test insert without test substance to be positioned between the areas with the different test substances. In addition, it is possible to use two or more test inserts, each of which are provided with a certain test substance.

According to a further advantageous embodiment, the lower layer and/or the covering layer of the pantyliner is provided with an opening via which the test strip insert can be introduced and positioned between covering layer and lower layer. This opening can be configured, for example, in the form of a slit. In addition, two or more openings may be provided.

Alternatively or additionally, the lower layer and/or the covering layer of the pantyliner can be formed in two sections and, for example, have sections which overlap. By unfolding the sections, the inside of the pantyliner can thus be freed and a test insert inserted. The two sections are then closed again.

Advantageously, such sections overlap and can also be joined together in a detachable and fixed-position manner by means of an adhesive layer and/or by means of a Velcro fastening.

In order to be able to see the inserted test insert through the covering layer even more easily and in order to be able to establish colour changes therein, it may be advantageous to arrange zones of increased transparency in the covering layer. In addition, zones of increased moisture permeability may be provided in order to achieve a response of the test substance with high certainty.

If the pantyliner consists of a washable and reusable material, it can be reused many times and is gentle on resources.

In this respect, the pantyliner can consist, for example, of cotton or a cotton blend. With such a pantyliner which can be reused many times, after each use, the test insert in each case can be removed and checked for a colour change in order, after the pantyliner has been washed, to introduce an unused test insert into the pantyliner in order to be able to continue medical monitoring.

Slipping or sliding of the test insert within the pantyliner, which is undesired and impairs wear comfort, can be avoided by fixing the test insert into the inside of the pantyliner. This may be done, for example, by sewing, pressing and/or pasting. In this connection, the test insert can, for example, be fixed on one or both sides in the edge regions of the pantyliner between the lower layer and the covering layer.

Figure 2:
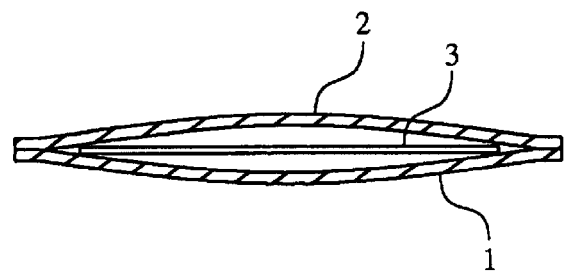
Figure 3:
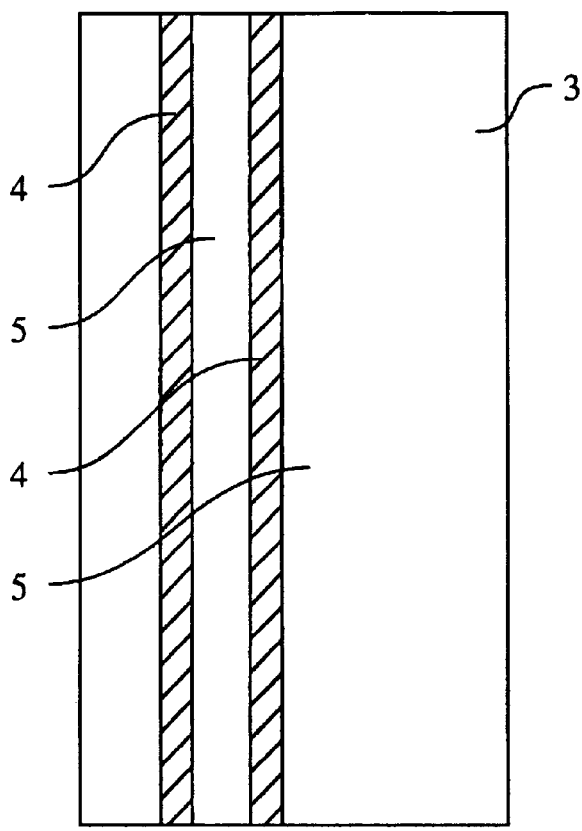
Figure 4:
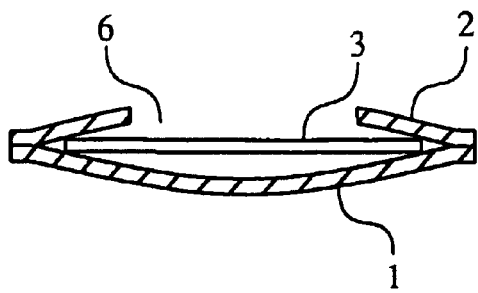
Figure 5:
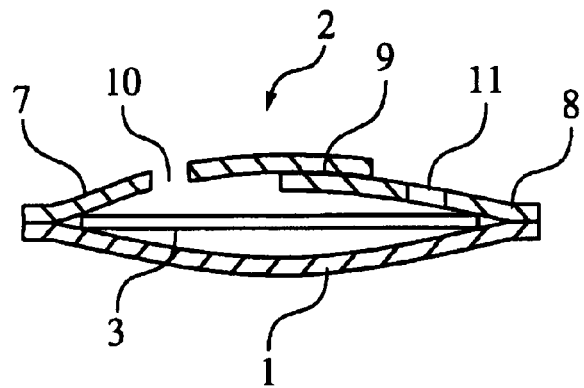

The invention is illustrated in more detail by reference to working examples in the schematic drawing figures. These show:

FIG. 1 a top view of a pantyliner according to the invention,

FIG. 2 a section II—II as in FIG. 1,

FIG. 3 a top view of a test strip insert,

FIG. 4 a section IV—IV as in FIG. 1,

FIG. 5 a section through a modified embodiment of the pantyliner and

Figure 6:
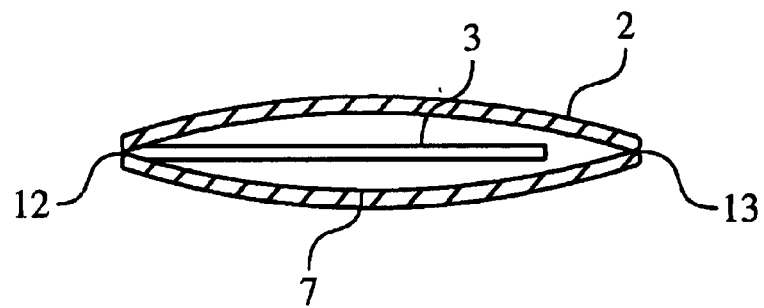

FIG. 6 a section through a further modified embodiment of a pantyliner.

In the top view according to FIG. 1, the pantyliner according to the invention is depicted with the covering layer 2 and the test insert 3 arranged below. The test strip insert 3 can be introduced and removed through the slit 6. The covering layer 2 has zones 10, 11 of increased transparency or moisture permeability (cf. FIG. 5). These zones 10, 11 may also be designed as indentations, which are designed to be particularly small in area, e.g. slit-like or punctiform, in order to minimize direct contact between the skin and the test insert 3.

It is clear from the sectional representation according to FIG. 2 that the test insert 3 is arranged between the moisture-permeable covering layer 2 and the moisture-impermeable lower layer 1. Secretions in the vaginal area penetrate the covering layer 2 and contact the test insert 3 so that the test substance of the test insert 3, where appropriate, reacts and changes colour. If a litmus insert is used as test insert 3, the amniotic fluid secreted in the case of premature amniorrhexis of a pregnant woman can be detected since a colour change in the test insert 3 (litmus paper) is ascertained as a result of the change in the pH in the vaginal area.

Due to the at least partial transparency of the covering layer 2 and/or the lower layer 1, this colour change in the test insert can be recognized by the pregnant woman herself. Alternatively or additionally, the test insert 3 can, for example, also be removed from the pantyliner through the slit 6 inserted in the end region (or at the side in longitudinal direction, not shown) of the pantyliner (cf. FIG. 1) in order to be able to see it more easily. Two or more test inserts 3 can also be inserted into the pantyliner (not shown).

In addition, it is possible to use test inserts 3 as in FIG. 3 which have first areas 4 which are provided with a test substance, and further areas 5 into which no test substance has been incorporated. In the areas 4 which are adjacent and which run, for example, in a strip-like manner, it is possible to introduce different test substances in order to be able to detect changes e.g. in the pH, the sugar or protein content.

FIG. 4 shows a sectional representation B—B as in FIG. 1 of the pantyliner in the region of the slit 6. In this region, the test insert 3 can be introduced between the covering layer 2 and the lower layer 1 of the pantyliner, or be pulled out of the pantyliner by intervention from the pregnant woman.

According to a first modification of the pantyliner as in FIG. 5, the covering layer 2 has sections 7, 8 which overlap and are detachably joined to one another in the overlapping area by means of an adhesive layer 9 (and/or a Velcro fastening).

If the pantyliner should then be opened, the sections 7, 8 of the covering layer 2 are detached from one another in the area of the adhesive layer 9, and the sections 7, 8 can be unfolded in order to insert or to remove a test insert 3.

The sections 7, 8 have zones 10 (indentations) and/or 11 (windows) of increased moisture permeability and/or increased transparency in order to reliably ensure that the secretions in the vaginal area also reach the test insert 3 and are visible. This may be advantageous particularly in the case of a pantyliner according to FIG. 5 since the sections 7, 8 of the covering layer 2 overlap and, in some circumstances, the moisture permeability and/or transparency of the covering layer 2 may be lower in the overlapping area.

In a further modified embodiment as in FIG. 6 of the pantyliner, the test insert 3 is fixed in edge regions 12 and/or 13 of the pantyliner between the covering layer 2 and the lower layer 1, e.g. by sewing, pressing and/or pasting. This avoids an unintentional sliding of the test strip insert 3 between the lower layer 1 and the covering layer 2.

What is claimed is:

1. Pantyliner, in particular for pregnant women, with a liquid-impermeable lower layer and a liquid-permeable covering layer, characterized in that a test insert (3) provided with a test substance is arranged between the lower layer (1) and the covering layer (2), characterized in that the lower layer (1) is formed in one section and the covering layer (2) is formed in two sections (7,8) which at least partially overlap, whereby the sections (7,8) are detachably joined to one another in the overlapping area by means of an adhesive layer (9).

2. Pantyliner according to claim 1, characterized in that the covering layer (2) is at least partially transparent or translucent for recognizing a color change in the test insert (3).

3. Pantyliner according to claim 1, characterized in that the test insert (3) is provided with at least one other test substance.

4. Pantyliner according to claim 1, characterized in that the test insert (3) is provided with a test substance for recognizing a change in the pH.

5. Pantyliner according to claim 1, characterized in that the test insert (3) has at least one first area (4) provided with a test substance, and at least one second area (5) without incorporated test substance.

6. Pantyliner according to claim 5, characterized in that the first area (4) and/or the second area (5) run essentially in a strip-like manner.

7. Pantyliner according to claim 1, characterized in that the lower layer (1) and/or the covering layer (2) have at least one opening for inserting and/or removing the test insert (3).

8. Pantyliner according to claim 7, characterized in that the opening is formed as a slit (6) in the lower layer (1) and/or in the covering layer (2).

9. Pantyliner according to claim 1, characterized in that the sections (7, 8) are detachably joined to one another by means of a hook and loop fastening.

10. Pantyliner according to claim 1, characterized in that the covering layer (2) has zones (10, 11) of increased moisture permeability.

11. Pantyliner according to claim 1, characterized in that the covering layer (2) has zones (10, 11) with an increased degree of transparency.

12. Pantyliner according to claim 1, characterized in that the pantyliner comprises a washable material which can be reused a number of times.

13. Pantyliner according to claim 12, characterized in that the pantyliner comprises cotton or a cotton blend.

14. Pantyliner according to claim 1, characterized in that the test insert (3) is arranged in a fixed manner between the lower layer (1) and the covering layer (2).

15. Pantyliner according to claim 14, characterized in that the test insert (3) is 25 joined to at least one edge region (12, 13) of the lower layer (1) and/or the covering layer (2).

16. Pantyliner according to claim 14, characterized in that the test insert (3) is sewn, pressed and/or pasted to the lower layer (1) and/or the covering layer (2) at least in some areas.

* * * * *

UNITED STATES PATENT AND TRADEMARK OFFICE
CERTIFICATE OF CORRECTION

| | | |
|---|---|---|
| PATENT NO. | : 6,982,360 B2 | Page 1 of 1 |
| APPLICATION NO. | : 10/182011 | |
| DATED | : January 3, 2006 | |
| INVENTOR(S) | : Buzluhan | |

It is certified that error appears in the above-identified patent and that said Letters Patent is hereby corrected as shown below:

Column 4, line 56 (Line 2 of Claim 15), after the word "is" please delete: "25".

Signed and Sealed this

Twentieth Day of February, 2007

JON W. DUDAS
*Director of the United States Patent and Trademark Office*